(12) United States Patent
Hayashi et al.

(10) Patent No.: US 10,794,896 B2
(45) Date of Patent: Oct. 6, 2020

(54) BLOOD COAGULATION SYSTEM EXAMINATION MODULE, BLOOD COAGULATION SYSTEM EXAMINATION SYSTEM, BLOOD COAGULATION SYSTEM EXAMINATION METHOD, AND DETERMINATION METHOD OF PARAMETER FOR BLOOD COAGULATION SYSTEM EXAMINATION MODULE

(71) Applicant: Sony Corporation, Tokyo (JP)

(72) Inventors: Yoshihito Hayashi, Chiba (JP); Marcaurele Brun, Tokyo (JP); Shinji Omori, Chiba (JP)

(73) Assignee: Sony Corporation, Tokyo (JP)

( * ) Notice: Subject to any disclaimer, the term of this patent is extended or adjusted under 35 U.S.C. 154(b) by 236 days.

(21) Appl. No.: 16/071,663

(22) PCT Filed: Nov. 16, 2016

(86) PCT No.: PCT/JP2016/083882
§ 371 (c)(1),
(2) Date: Jul. 20, 2018

(87) PCT Pub. No.: WO2017/130528
PCT Pub. Date: Aug. 3, 2017

(65) Prior Publication Data
US 2019/0017995 A1 Jan. 17, 2019

(30) Foreign Application Priority Data
Jan. 29, 2016 (JP) .................... 2016-015444

(51) Int. Cl.
*G01N 33/86* (2006.01)
*G01N 33/49* (2006.01)
*G01N 27/22* (2006.01)

(52) U.S. Cl.
CPC ....... *G01N 33/4905* (2013.01); *G01N 27/221* (2013.01); *G01N 33/86* (2013.01)

(58) Field of Classification Search
CPC ... G01N 33/4905; G01N 33/86; G01N 27/221
See application file for complete search history.

(56) References Cited

U.S. PATENT DOCUMENTS

| 5,192,689 A | 3/1993 | Hemker et al. |
| 8,551,722 B2 | 10/2013 | Hemker et al. |

(Continued)

FOREIGN PATENT DOCUMENTS

| JP | 2010-181400 A | 8/2010 |
| JP | 2014-169920 A | 9/2014 |

(Continued)

OTHER PUBLICATIONS

International Search Report and English translation thereof dated Dec. 27. 2016 in connection with International Application No. PCT/JP2016/083882.

(Continued)

*Primary Examiner* — Jennifer Wecker
*Assistant Examiner* — Michael Paul Shimek
(74) *Attorney, Agent, or Firm* — Wolf, Greenfield & Sacks, P.C.

(57) ABSTRACT

Disclosed are a blood coagulation system examination module, a blood coagulation system examination system, and a blood coagulation system examination method, all of which enable to simply and easily measure thrombin potential with a whole blood sample.
The blood coagulation system examination module includes a thrombin potential examination unit configured to examine thrombin potential on the basis of an electrical property of blood as measured at a specific frequency and predetermined (Continued)

time intervals in a predetermined period after reversal of an anticoagulation action working on the blood.

10 Claims, 10 Drawing Sheets

(56) References Cited

U.S. PATENT DOCUMENTS

| | | |
|---|---|---|
| 8,916,356 B2 | 12/2014 | Hemker et al. |
| 2012/0035450 A1 | 2/2012 | Hayashi |
| 2014/0248259 A1 | 9/2014 | Camire |
| 2015/0077144 A1* | 3/2015 | Hayashi ................ G01N 27/06 324/693 |

FOREIGN PATENT DOCUMENTS

| | | |
|---|---|---|
| JP | 2015-501137 A | 1/2015 |
| WO | WO 2013/049804 A1 | 4/2013 |

OTHER PUBLICATIONS

International Written Opinion and English translation thereof dated Dec. 27, 2016 in connection with International Application No. PCT/JP2016/083882.

International Preliminary Report on Patentability and English translation thereof dated Aug. 9, 2018 in connection with International Application No. PCT/JP2016/083882.

Extended European Search Report dated Dec. 19, 2018 in connection with European Application No. 16888113.4.

* cited by examiner

FIG. 9
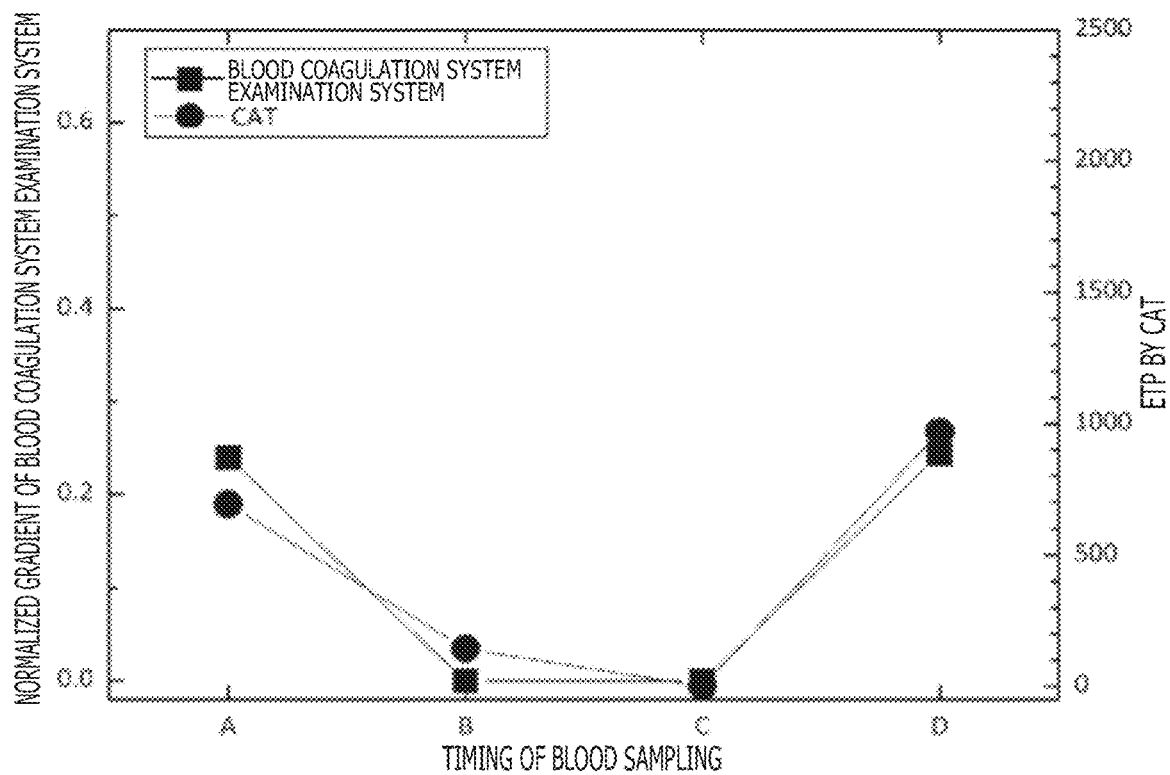
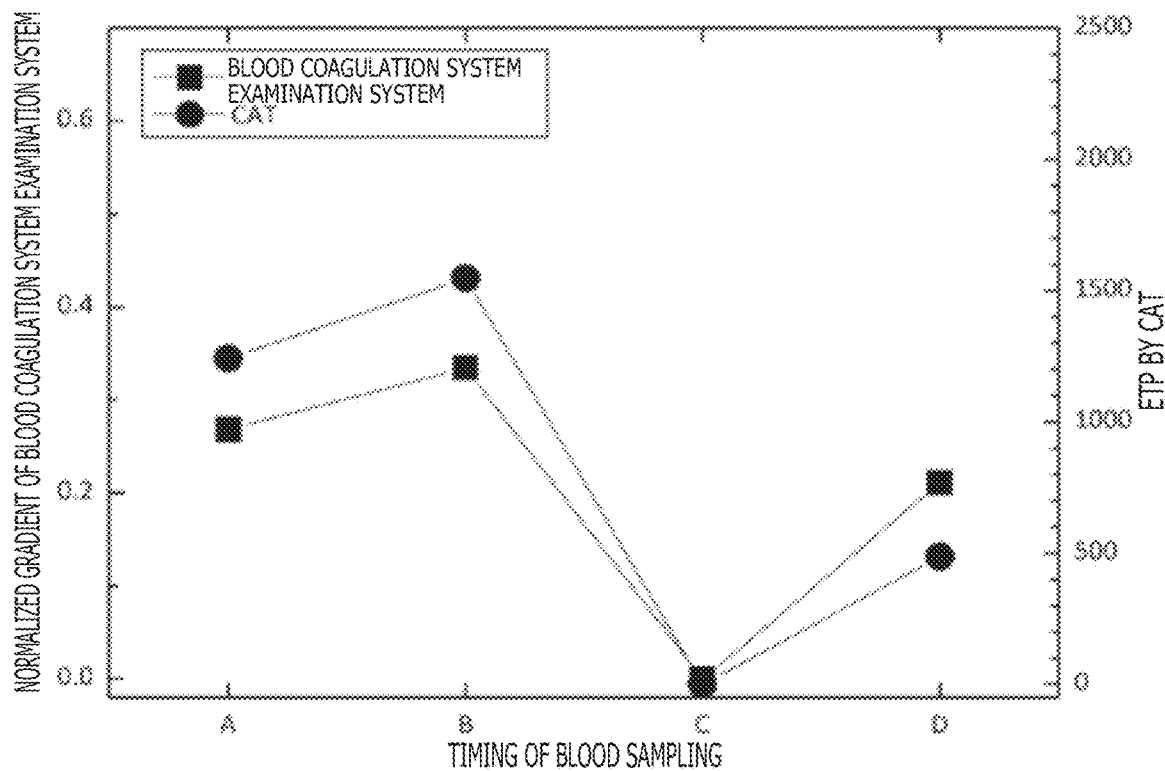

FIG.10
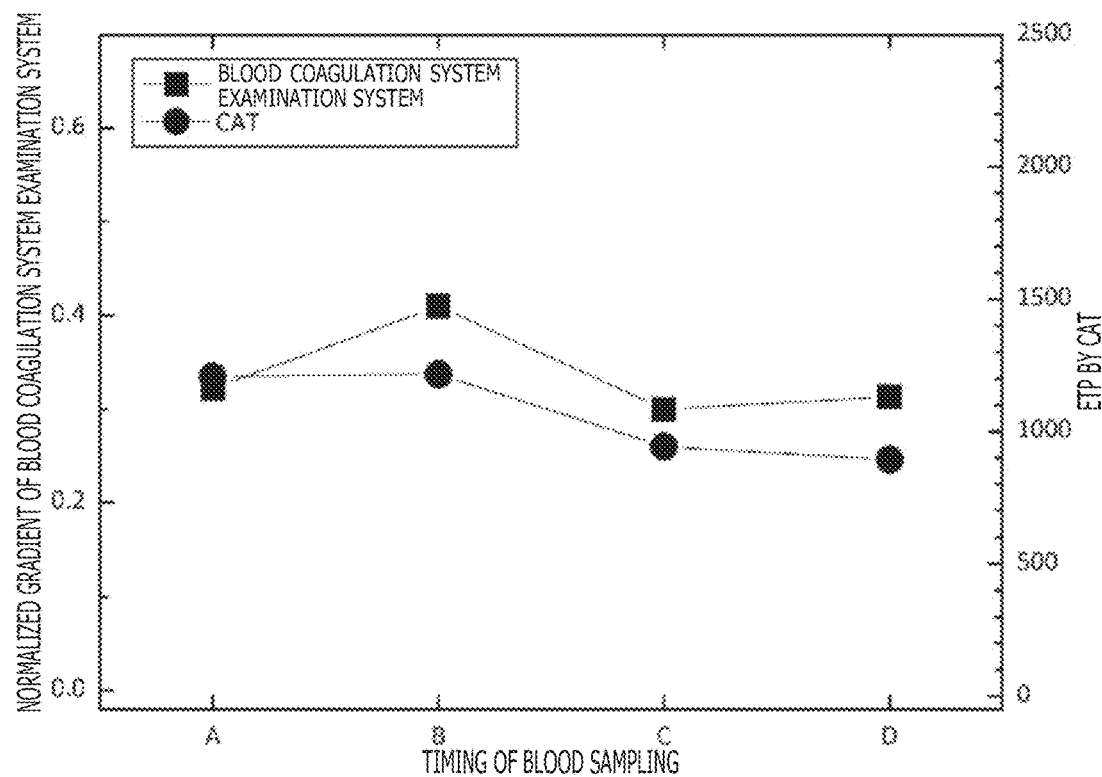
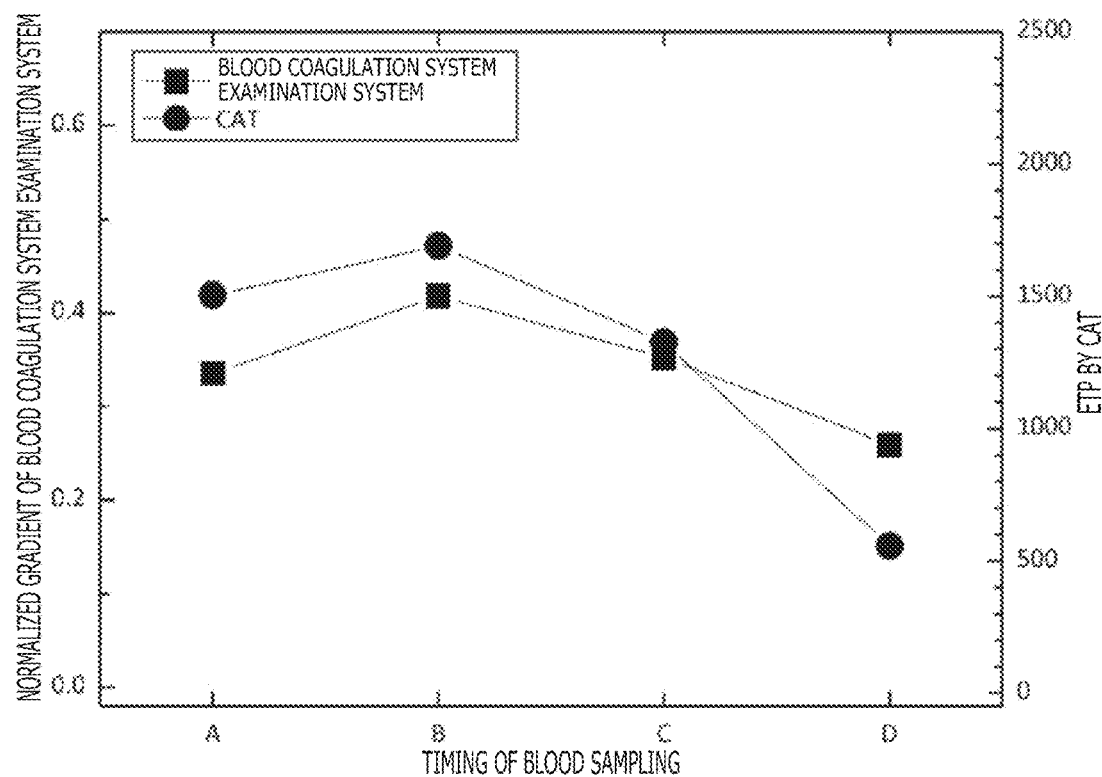

BLOOD COAGULATION SYSTEM EXAMINATION MODULE, BLOOD COAGULATION SYSTEM EXAMINATION SYSTEM, BLOOD COAGULATION SYSTEM EXAMINATION METHOD, AND DETERMINATION METHOD OF PARAMETER FOR BLOOD COAGULATION SYSTEM EXAMINATION MODULE

CROSS REFERENCE TO RELATED APPLICATIONS

This is a U.S. National Stage Application under 35 U.S.C. § 371, based on International Application No. PCT/JP2016/083882, filed Nov. 16, 2016, which claims priority to Japanese Patent Application JP 2016-015444, filed Jan. 29, 2016, each of which is hereby incorporated by reference in its entirety.

TECHNICAL FIELD

The present disclosure relates to a blood coagulation system examination module, a blood coagulation system examination system, a blood coagulation system examination method, and a determination method of a parameter for the blood coagulation system examination module.

BACKGROUND ART

Thrombogenesis (coagulation) and thrombolysis (fibrinolysis) in an organism proceed through a complex cascade reaction, and both many molecular components, including coagulation factors, fibrinogen and fibrin, and cell components such as vascular endothelial cells and platelets take part in the reaction. In the treatment or prevention of a disease or injury involving coagulation and fibrinolysis, various tests are conducted to assess the patient's blood clotting ability and fibrinolytic ability. These clotting and fibrinolytic tests can be divided roughly into quantitative tests and function tests. The quantitative tests measure the quantities of particular molecules that take part in the coagulation and fibrinolysis reaction system, such as various coagulation factors, fibrinogen and D-dimer. On the other hands, the function tests assess the degree of activity of the entirety or a part of the reaction system.

The coagulation reaction system is divided into a mechanism (exogeneous system) that is triggered by the formation of a complex between tissue factor and activated coagulation factor VII and a mechanism (endogeneous system) that is triggered by activation of factor XII through a contact or the like with foreign matter. These mechanisms merge together at the stage of activation of factor X.

It is to be noted that following the custom in the thrombosis and hemostasis field, each coagulation factor will hereinafter be represented by placing "F" before the Roman numeral as its factor number and that, if it has been activated, "a" will hereinafter be added to the end. For example, factor XII and activated factor VII will be represented as "FXII" and "FVIIa," respectively.

Formed FXa activates prothrombin (FII) to convert it into thrombin (FIIa), and under the action of thrombin, fibrinogen is converted into fibrin. Formed fibrin molecules polymerize together into hardly-soluble, high molecular strands, followed by the formation of a three-dimensional network structure called "stabilized fibrin" under the action of FXIIIa and platelets. A structure with erythrocytes primarily entangled in the network structure is a thrombus. Once a thrombus is formed, the fibrinolysis reaction system begins to act so that coagulation is prevented from proceeding too much. The thrombus that has finished its role of hemostasis will be dissolved in due time.

As function tests for exogeneous clotting ability and endogeneous clotting ability, prothrombin time (PT) and activated partial thromboplastin time (APTT) are in wide use, respectively. In these tests, substances that induce the exogeneous and endogeneous coagulation reactions (for example, tissue factor and ellagic acid, respectively) are added in large excess so that test results can be obtained in a short time. Normal values of prothrombin time and activated partial thromboplastin time are approximately 10 seconds and 30 to 40 seconds, respectively. Therefore, these tests are suited for the assessment of a significant reduction of clotting ability, in other words, bleeding tendency, but in contrast, are not suited for the assessment of significant proceeding of clotting ability, in other words, clotting tendency or subtle changes of clotting ability.

Other function tests include thromboelastography and thromboelastometry, which have been put to practical use as "TEG® 5000" (Haemonetics Corporation) and "ROTEM® delta" (TIM Innovations), respectively. With TEG 5000, a whole blood sample is charged in a cup as a measurement container, and subsequent to addition of an inducing substance corresponding to the purpose of the test, a rod-shaped pin suspended by a wire from an upper part of the container is dipped and a steady reciprocal angular motion (a motion that reciprocates typically in a range of 4.45° in 10 seconds) is applied to the container. As the coagulation reaction proceeds, the viscoelasticity of the sample increases, so that the relative motion between the cup and the pin decreases and the rotational displacement of the pin increases accordingly. By recording this rotational displacement over time with an optical system included in the analyzer, a waveform called a thromboelastogram is obtained. ROTEM delta is also based fundamentally on the same principle as TEG 5000 although there is a difference in that a reciprocal angular motion is applied to the pin instead of the cup. The above-described prothrombin time and activated partial thromboplastin time are end-point detection methods of coagulation, while thromboelastography and thromboelastometry have a merit that allows to perform, with a single analyzer, monitoring of a series of processes from the initiation of coagulation to thrombogenesis, and further to the subsequent fibrinolysis.

Thromboelastography and thromboelastometry place a focus on the generation of fibrin as the final stage of the coagulation cascade reaction, and through the viscoelasticity of a sample, perform monitoring of the process from the formation of networks of fibrin (coagulation) to thrombolysis (fibrinolysis). Thromboelastography and thromboelastometry can, therefore, be considered to comprehensively assess the activity of the entire reaction system up to the generation of fibrin.

On the other hand, there is also thrombin generation test (TGT) that places a focus on the generation of thrombin, which is one stage before the generation of fibrin, and is intended to comprehensively assess the action of the entire reaction system until proceeding to the generation of thrombin. In a thrombin generation test, tissue factor in an amount (for example, 5 pM or so) far smaller than that required for prothrombin time is added to a sample to induce an exogeneous coagulation reaction in a relatively gentle manner, and the amount of thrombin to be generated is measured over time.

Thrombin is serine protease (a proteolytic enzyme having a serine residue), recognizes a specific amino acid sequence, and cleaves peptide bonds. Utilizing this property, thrombin can be detected with a synthetic substrate in which a dye or a fluorescent substance is bound on a peptide formed of three to four amino acids. It is known that, when thrombin acts on a synthetic substrate called "Z-Gly-Gly-Arg-AMC," for example, the peptide bond between Arg and AMC is specifically cleaved and the liberated AMC emits fluorescence. Here, Z represents a benzyloxycarbonyl group, Arg represents arginine, Gly represents glycine, and AMC represents 7-amino-4-methylcoumarin. With the addition of an improvement to the correction of fluorescent signals (PTL 2), TGT (PTL 1) which is based on the synthetic substrate method has been put to practical use as a calibrated automated thrombogram (CAT) system (Thrombinoscope Bv). Calibrated automated thrombogram is one embodiment of the thrombin generation test.

In the two patent literature described above, not only plasma but also whole blood are included as test objects. In view of the principle that the development of a color in association with degradation of a synthetic substrate is optically detected, however, it is readily presumable that the TGT analyzer and CAT system would be restricted to plasma samples. Although a resolution method has been proposed for the problems specific to whole blood samples, i.e., low erythrocyte sedimentation rate (ESR) and low visible light transmittance (PLT 3), none has yet been put to practical use as a whole blood TGT analyzer that is routinely usable in clinical practice. The above-described, commercially-available, calibrated automated thrombogram system also requires platelet-poor plasma (PPP) or platelet-rich plasma (PRP) as a sample.

To conduct a thrombin generation test at present, plasma components alone must, therefore, be extracted by centrifugation from blood sampled from a patient. This pre-treatment generally requires time as much as several tens of minutes or longer. This leads to a significant obstacle when attempting to use a thrombin generation test as a test under a situation where swiftness is required. Examples of such a situation include a scene where, in a perioperative period of a surgery that may be accompanied by massive hemorrhage such as coronary artery bypass grafting using a heart-lung machine, a cause of unexpected, continued bleeding is ascertained in an attempt to make an appropriate determination on blood transfusion.

From the achievements of basic research in the thrombosis and hemostasis field, it has become evident that not only various molecular components, led by coagulation factors, in plasma but also cellular components such as platelets and erythrocytes take significant roles in the coagulation and fibrinolysis cascade reaction. A picture of such a coagulation and fibrinolysis reaction may also be called a "cell-based model." Therefore, the thrombin potential of a plasma sample from which cellular components have been eliminated cannot be absolutely considered to reflect the comprehensive coagulation pathophysiology of the patient.

CITATION LIST

Patent Literature

[PTL 1]
 U.S. Pat. No. 5,192,689
[PTL 2]
 U.S. Pat. No. 8,551,722
[PTL 3]
 U.S. Pat. No. 8,916,356

SUMMARY

Technical Problems

From the foregoing elucidation, the measurement of thrombin potential, if simply and easily applicable to a whole blood sample not subjected to the pre-treatment, is considered to be extremely useful as a test under a situation where swiftness and an accurate grasp of a comprehensive coagulation pathophysiology are required as in a perioperative period or emergency medical practice.

Further, in thromboelastography and thromboelastometry mentioned above, changes in a blood property in a measurement container are measured as changes in viscoelasticity. However, it is not certain at all if information similar to that available by the calibrated automated thrombogram method, which directly detects thrombin molecules themselves as generated by an inducing substance, is available from changes in such a physical property.

With the foregoing in view, the inventors of this application conceived that, for a whole blood sample to which an application of a measurement method using light is restricted, it would be effective to measure, as changes in a physical property, changes in a blood property as associated with coagulation and fibrinolysis, and as a result of extensive research, have completed this technology.

Solution to Problems

Described specifically, this technology provides a blood coagulation system examination module including a thrombin potential examination unit configured to examine thrombin potential on the basis of an electrical property of blood as measured at a specific frequency and predetermined time intervals in a predetermined period after reversal of an anticoagulation action working on the blood.

The thrombin potential examination unit may be configured to analyze a correspondence relationship between the electrical property of the blood, which has measured at the specific frequency in the predetermined period, and the thrombin potential and to examine thrombin potential of target blood from the electrical property of the target blood on the basis of the correspondence relationship.

The thrombin potential examination unit may be configured to examine the thrombin potential on the basis of a value $G_{max}/A_{max}$ obtained by dividing a maximum gradient $(G_{max})$ of a waveform of the electrical property at the specific frequency in the predetermined period with a maximum amplitude $(A_{max})$ of the waveform of the electrical property at the specific frequency in the predetermined period.

In this technology, the blood may contain tissue factor added thereto to have a concentration of 0.5 pM or higher but 1 pM or lower.

The specific frequency may be 1 kHz or higher but 50 MHz or lower.

Further, this technology also provides a blood coagulation system examination system including:
 a pair of electrodes,
 an application unit that applies an alternating voltage at predetermined time intervals across the pair of electrodes,
 a measurement unit that measures an electrical property of blood placed between the pair of electrodes, and
 a thrombin potential examination unit configured to examine thrombin potential on the basis of the electrical property measured at a specific frequency and the predetermined time intervals in a predetermined period after reversal of an anticoagulation action working on the blood.

The blood coagulation system examination system according to this technology may further include an output unit that outputs information associated with the thrombin potential as examined by the thrombin potential examination unit.

The blood coagulation system examination system may further include a warning unit that generates a warning when a result of the examination of the thrombin potential by the thrombin potential examination unit deviates from a preset normal value.

Furthermore, this technology also provides a blood coagulation system examination method including:

applying an alternating voltage at predetermined time intervals across a pair of electrodes, measuring an electrical property of blood placed between the pair of electrodes, and examining thrombin potential on the basis of the electrical property measured at a specific frequency and the predetermined time intervals in a predetermined period after reversal of an anticoagulation action working on the blood.

Still furthermore, this technology also provides a determination method of a parameter for a blood coagulation system examination module, which includes:

applying an alternating voltage at predetermined time intervals across a pair of electrodes, measuring an electrical property of blood placed between the pair of electrodes, and determining the parameter for examination of thrombin potential by comparing data, which are obtained from the electrical property measured at a specific frequency and the predetermined time intervals in a predetermined period after reversal of an anticoagulation action working on the blood, with data obtained in a known test on the thrombin potential.

Advantageous Effects of Invention

According to this technology, thrombin potential can be promptly, simply and easily measured using a whole blood sample.

It is, however, to be noted that advantageous effects of this technology are not necessarily limited to the one described above but can also include any one or ones of those to be described in this disclosure.

BRIEF DESCRIPTION OF DRAWINGS

FIG. 9 presents graphs each illustrating a comparison between data by the blood coagulation system examination system according to this technology and data by calibrated automated thrombogram.

FIG. 10 presents graphs each illustrating a comparison between data by the blood coagulation system examination system according to this technology and data by calibrated automated thrombogram.

DESCRIPTION OF EMBODIMENTS

Figure 1:
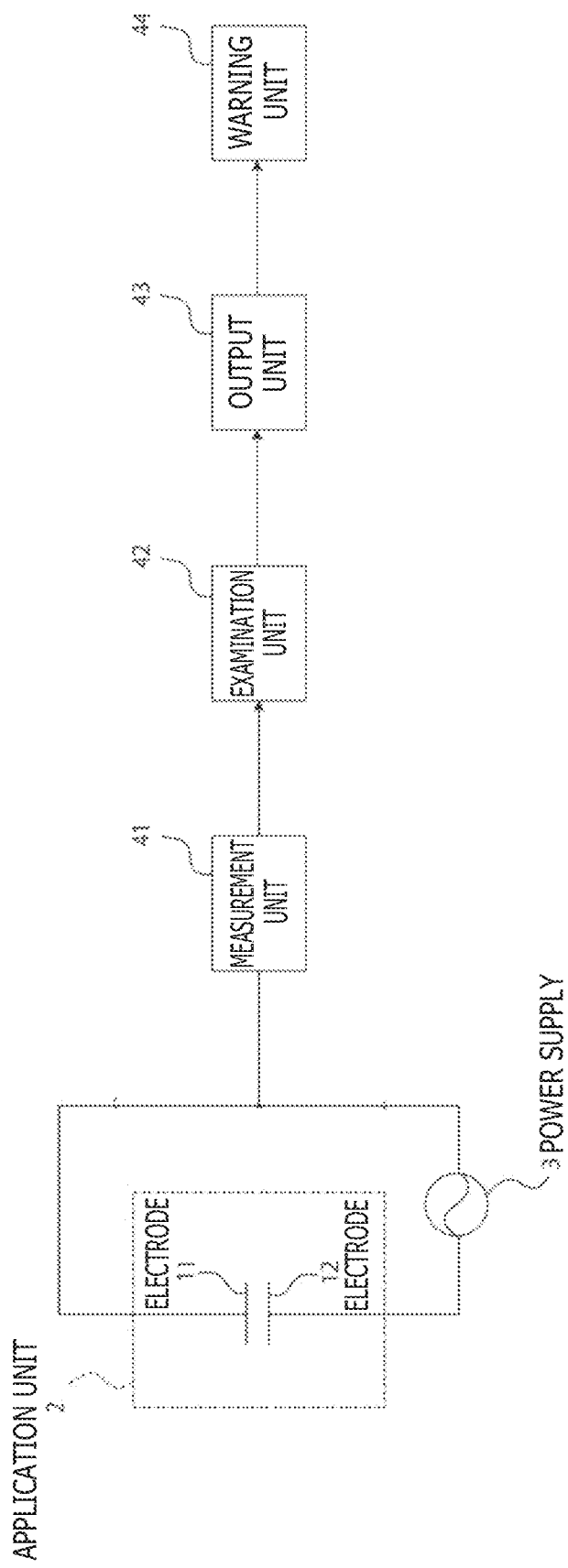
FIG. 1 is a schematic diagram depicting the configuration of a blood coagulation system examination system according to this technology.

Preferred embodiments for practicing this technology will hereinafter be described. It is to be noted that the embodiments to be described hereinafter illustrate representative embodiments of this technology and the scope of this technology shall not be narrowly interpreted by the embodiments. The description will be made in the following order.
1. Blood Coagulation System Examination Module and System
  1-1. Configurations of Module and System
  1-2. Operation of System
2. Blood Coagulation System Examination Procedures
3. Examination Procedures for Thrombin Potential
4. Determination of Parameter of Thrombin Potential
5. Embodiment
  5-1. Embodiment of Blood Coagulation System Examination Procedures
  5-2. Determination of Parameter Correlated to Thrombin Potential
  5-3. Determination of Calibration Line and Normal Range
  5-4. Summary 1. Blood Coagulation System Examination Module and System 1-1. Configurations of Module and System The blood coagulation system examination module according to this technology includes a thrombin potential examination unit configured to examine thrombin potential on the basis of an electrical property. Additional inclusion of a pair of electrodes, a power supply, an application unit that applies an alternating voltage across the pair of electrodes, and a measurement unit that measures the electrical property of blood can provide a system. It is possible to still additionally include an output unit and a warning unit. The configuration of the blood coagulation system examination system is depicted in FIG. 1.

1-2. Operation of System

First, blood is placed between a pair of electrodes 11 and 12. The blood can be placed between the electrodes 11 and 12, for example, by filling it in a sample cartridge beforehand and fitting the sample cartridge on an electrode part. Further, an anticoagulation treatment reversing agent or the like may be added when placing the blood. The addition of the chemical agent can be conducted by providing the sample cartridge with a chemical agent inlet.

As the blood, it is common to use blood sampled from a vein by using citric acid or the like as an anticoagulant. In this technology, an anticoagulation action is reversed with an anticoagulation treatment reversing agent such as an aqueous solution of calcium chloride shortly before the initiation of measurement of the electrical property, and the measurement is conducted in a state that the blood coagulation reaction is in progress.

A coagulation reaction inducing agent for use in this technology is not particularly limited, and can be, for example, a tissue factor.

In a conventional thrombin generation test (TGT), tissue factor as much as, for example, 5 pM or so is added to a sample as mentioned above. In this technology, on the other hand, it is only necessary to add, to a sample, tissue factor in such a small amount as providing a concentration of 0.5 pM to 1 pM, for example. In this concentration range, the correlation between the below-described endogenous thrombin potential (ETP) and the result of measurement by the blood coagulation system examination system are presumed to be particularly good.

A power supply 3 applies a voltage taking, as a starting time point, the time point at which a command to begin a measurement has been received or the time point at which the power supply has been turned on. Specifically, the power supply 3 applies an alternating voltage of a predetermined frequency at every preset measurement interval across the electrodes 11 and 12 arranged in an application unit 2.

Next, a measurement unit 41 measures a current or impedance across the electrodes 11 and 12 in a preset cycle, and from the measurement values, derives the permittivity at the specific frequency. For the derivation of the permittivity, a known function or relational expression that represents a relationship between current or impedance and permittivity is used.

The permittivity can be measured using an impedance analyzer "4294A" manufactured by Agilent Technologies or the like. The specific frequency may be preferably 1 kHz or higher but 50 MHz or lower, more preferably 1 MHz or higher but 10 MHz or lower. According to a measurement at 1 MHz or 10 MHz frequency, the derived permittivity is presumed to correlate well with endogenous thrombin potential (ETP) to be described subsequently herein.

The measurement interval of the preset cycle can be, for example, every 1 minute, and the sample as a measurement target can be measured under the temperature condition of 37° C.

The data of permittivity is fed at every measurement interval from the measurement unit 41 to an examination unit 42, and upon receipt of the data of permittivity fed from the measurement unit 41, the examination unit 42 begins an assessment or the like of the coagulation potential of the blood. The examination unit 42 includes a thrombin potential examination unit, and the thrombin potential examination unit analyzes a correspondence relationship between the electrical property of the blood as measured at the specific frequency in a predetermined period and the thrombin potential and examines the thrombin potential from the electrical property of the target blood on the basis of the correspondence relationship. The examination unit 42 can notify one or both the examination result such as the assessment of thrombin potential and the data of permittivity to an output unit 43. The data or the like can be presented as a graph of waveform or the like, and various parameters can be derived from the waveform.

The output unit 43 receives the examination result and the data or the like of the permittivity from the examination unit 42, and displays them on a monitor or prints them on a predetermined medium.

A range of normal values of thrombin potential or the like has been incorporated beforehand in the examination unit 42. If the measurement result falls outside the range of normal values, a notification is made to the output unit 43 accordingly, and in addition, information is transmitted from the output unit 43 to a warning unit 44 to the effect that an abnormal value has been detected.

The warning unit 44 can notify a warning to a system operator by a measure such as monitor display, warning sound or warning lamp lighting.

2. Blood Coagulation System Examination Procedures

Blood coagulation system examination procedures to be performed in this technology can be carried out using, for example, the blood coagulation system examination system described in the specification of Japanese Patent No. 5,691,168 or the specification of Japanese Patent No. 5,768,422.

Figure 2:
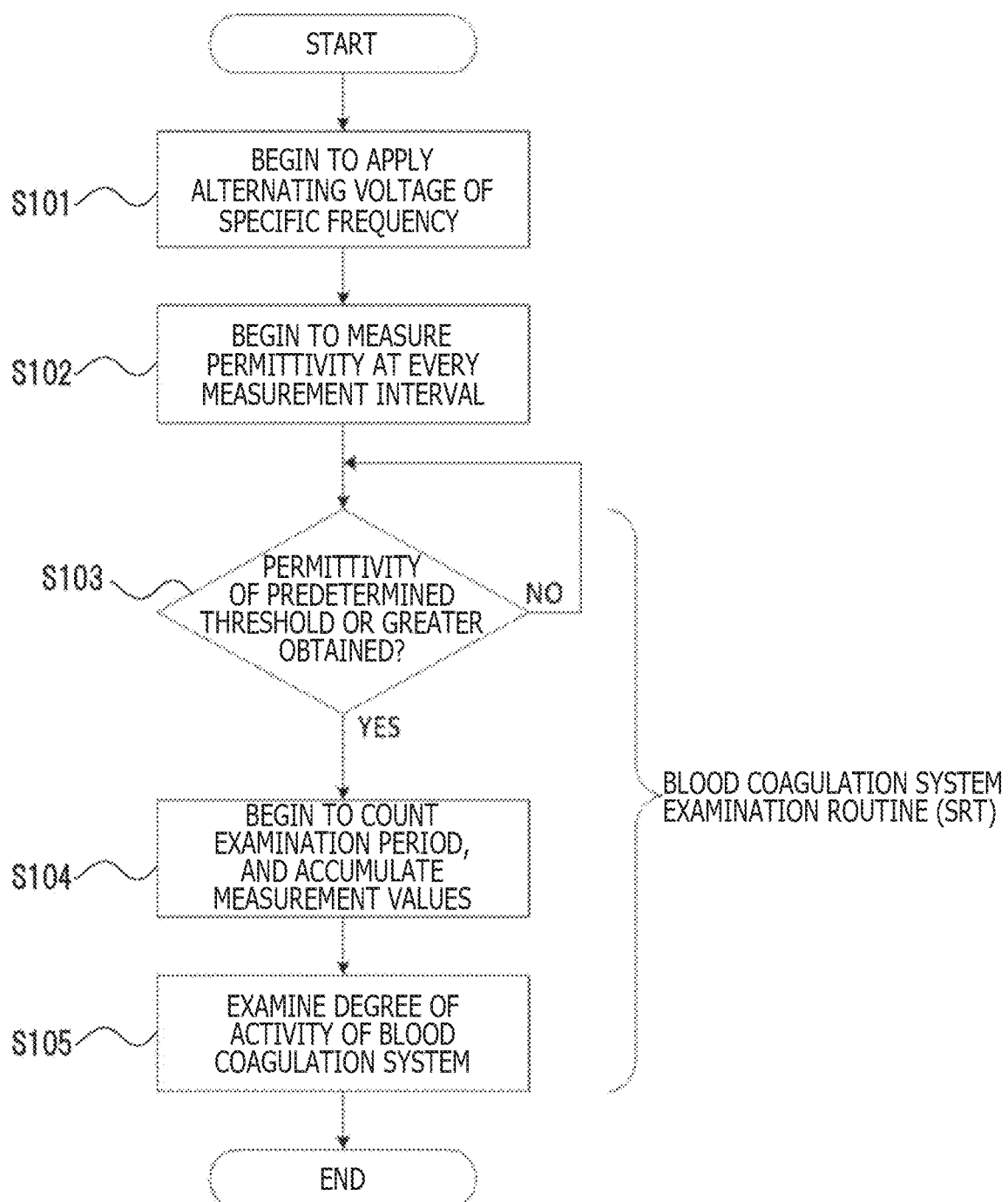
FIG. 2 is a flow chart illustrating blood coagulation system examination procedures according to this technology.

Blood coagulation system examination procedures that use the above-mentioned system are illustrated in FIG. 2.

The blood coagulation system examination system described in either specification applies an alternating voltage of a specific frequency at predetermined time intervals across electrodes if a measurement unit receives a command to begin a measurement or if a power supply is turned on (S101).

Next, the measurement unit begins to measure the permittivity of blood placed between the electrodes at every measurement interval (S102). Subsequently, the processing proceeds to the following subroutine (SRT, which may hereinafter be also called "the blood coagulation system examination subroutine").

In the blood coagulation system examination subroutine (SRT), an examination unit first awaits permittivity data indicating a permittivity that is equal to greater than a predetermined threshold (S103). If permittivity data equal to or greater than the predetermined threshold is received (YES), the examination unit takes it as a time point that an anticoagulation action on the blood has been reversed, and the processing proceeds to the next step. If permittivity data smaller than the predetermined threshold is received (NO), the examination unit determines that the anticoagulation action on the blood has not been reversed, and the measurement is continued.

In addition, the examination unit also begins to count a preset examination period, and accumulates data of permittivity, which are fed from the measurement unit, until the examination period elapses (S104).

Then, the examination unit detects a straight line that is most approximate, for example, to the permittivity indicated by the data of permittivity accumulated during the examination period, and examines the degree of activity of the blood coagulation system by using the gradient or the like of the straight line as a parameter (S105).

It is to be noted that no limitation is imposed on the measurement and examination items of a blood coagulation system to which this technology can be applied and that illustrative measurement and examination items include, for example, blood coagulation (blood clotting), fibrination, fibrin clot formation, blood clot formation, erythrocyte rouleaux formation, blood aggregation, erythrocyte sedimentation (ES), clot shrinkage (retraction), hemolysis, fibrinolysis, and so on.

A description will hereinafter be made about a case in which the measurement item is thrombin potential.

3. Examination Procedures for Thrombin Potential

An outline of examination procedures for thrombin potential according to this technology is as follows.

First, specific data processing is applied to the characteristics of changes in electrical property, which are associated with the coagulation and fibrinolysis reaction of blood. A parameter is then determined, in terms of which the processed data and the thrombin potential available from the thrombin generation test (TGT) correlate well with each other. Next, the electrical property of the whole blood sample is measured, the measurement results are examined on the basis of the parameter, and the thrombin potential of the whole blood sample is determined.

Figure 3:
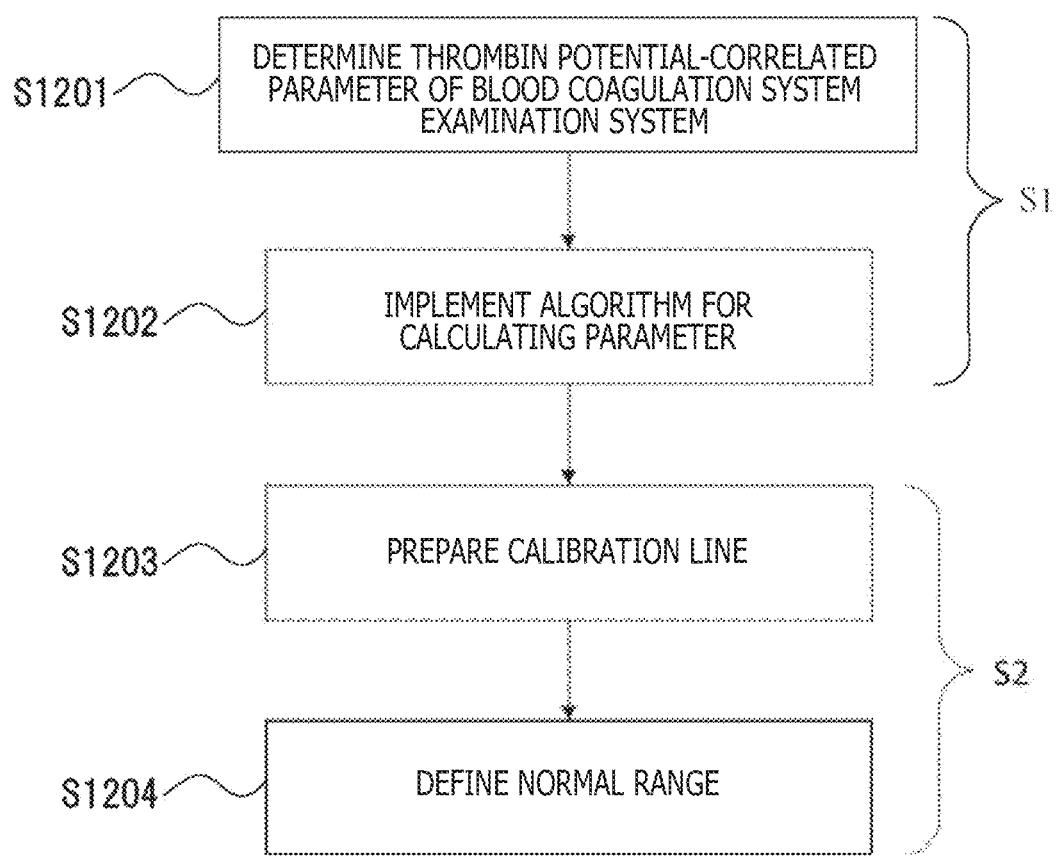
FIG. 3 is a flow chart of preparation procedures for examining thrombin potential according to this technology.

In further detail, prior to the examination procedures for thrombin potential, preparation procedures (Step 1 and Step 2 to be described subsequently herein) by a clinical study are first performed (FIG. 3) to set a new additional examination measure.

Step 1 (S1):

In the clinical study, data of both the thrombin generation test and the blood coagulation system examination system are collected for many samples. The examination unit compares and studies both of them, whereby at least one correlated combination of output parameters of the thrombin generation test and blood coagulation system examination system is determined (S1201). In addition, an algorithm for the calculation of the determined parameters is implemented in examination software of the blood coagulation system examination system (S1202).

Step 2 (S2):

On the basis of the data of the clinical study, the examination unit prepares a calibration line for converting the parameter of the blood coagulation system examination system into the parameter of the thrombin generation test (TGT) (S1203). Further, normal ranges of the parameters of the blood coagulation system examination system and thrombin generation test are defined (S1204). The data of the calibration line and normal ranges are incorporated as a database, which the examination software of the blood coagulation system examination system refers to in the course of processing, in a data examination software system.

By proceeding through Step 1 and Step 2 described above, new additional examination procedures can be set, and can be incorporated before the following blood coagulation system examination procedures (S3).

Figure 4:
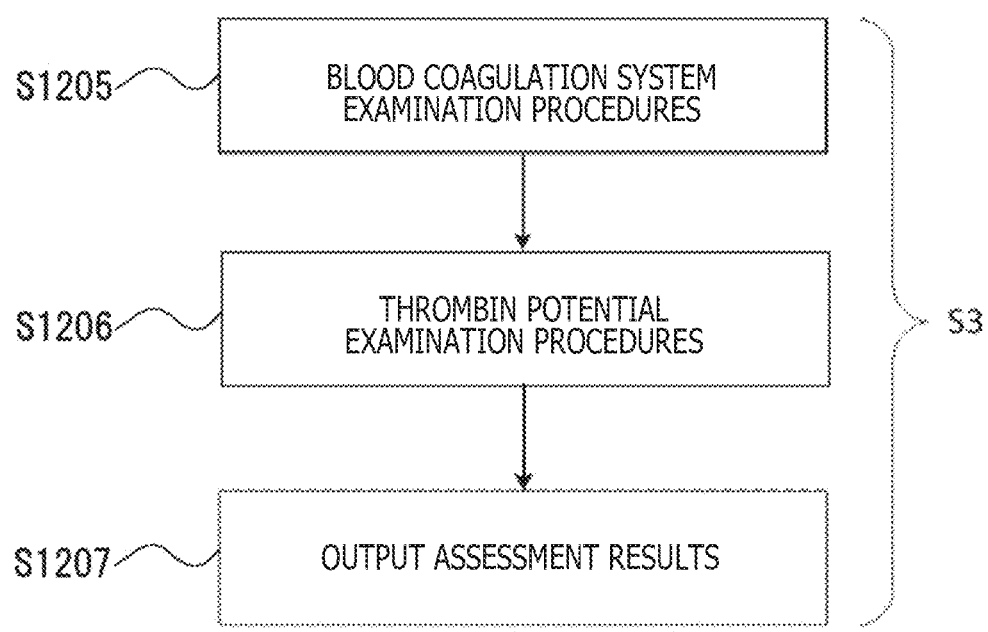
FIG. 4 is a flow chart of examination procedures including an examination of thrombin potential according to this technology.

Step 3 (S3):

In FIG. 4, examination procedures including an examination of thrombin potential is illustrated (S3).

In Step 3, a sample is measured by the blood coagulation system examination system, and the examination of its blood coagulation system is conducted at the examination unit (S1205). This part is common among measurement items of the blood coagulation system.

In addition, the examination unit calculates the parameter, which correlates with the thrombin generation test, by the algorithm newly added through Step 1 (S1206). Referring to the database, the examination unit also converts the parameter to the parameter of the thrombin generation test, and assesses whether the value is included within the normal range or is an abnormal value. From the output unit, the assessment result is outputted, for example, is displayed on a monitor or printed on a medium (S1207).

Once the examination procedures for thrombin potential can be established on the basis of the preparation procedures (S1 and S2) by the clinical study as mentioned above (S1206), it is no longer necessary to repeat the preparation procedures (S1 and S2), and examinations can be routinely performed in accordance with the blood coagulation system examination procedures (S3).

It is to be noted that the series of flow through Step 1, Step 2 and Step 3 is not limited to the examination of thrombin potential according to this technology.

4. Determination of Parameter for Thrombin Potential

In this technology, a parameter for the examination of thrombin potential is set beforehand in the examination unit.

The parameter is obtained, for example, by analyzing a correspondence relationship between the permittivity of blood as measured at a specific frequency in a predetermined period and the data of thrombin potential as obtained in a known test.

As the known test, at least one of, for example, thrombin generation test, prothrombin time, activated partial thromboplastin time, thromboelastography and thromboelastometry is selected.

On the other hand, data of the permittivity for determining a correspondence relationship with the date of the known test may include, for example, the followings:

The maximum gradient ($G_{max}$) of a waveform of the electrical property at a specific frequency in a predetermined period, the time ($T_{Gmax}$) to the maximum gradient of the waveform of the electrical property at the specific frequency in the predetermined period, the maximum amplitude ($A_{max}$) of the waveform of the electrical property at the specific frequency in the predetermined period, the time ($T_{Amax}$) to the maximum amplitude of the waveform of the electrical property at the specific frequency in the predetermined period, the minimum gradient ($G_{min}$) of the waveform of the electrical property at the specific frequency in the predetermined period, the time ($T_{Gmin}$) to the minimum gradient of the waveform of the electrical property at the specific frequency in the predetermined period, the minimum amplitude ($A_{min}$) of the waveform of the electrical property at the specific frequency in the predetermined period, the time ($T_{Amin}$) to the minimum amplitude of the waveform of the electrical property at the specific frequency in the predetermined period, and the coagulation start time (CT), And one of these data may be selected, or plural ones of these data may be selected and subjected to an arithmetic operation.

Illustrative of parameters obtained by such an arithmetic operation can be the value $G_{max}/A_{max}$ obtained by dividing the maximum gradient ($G_{max}$) of the waveform of the electrical property at the specific frequency in the predetermined period with the maximum amplitude ($A_{max}$) of the waveform of the electrical property at the specific frequency in the predetermined period.

5. Embodiment

An illustrative embodiment will hereinafter be described, although this technology shall not be limited to the embodiment.

5-1. Embodiment of Blood Coagulation System Examination Procedures

Figure 5:
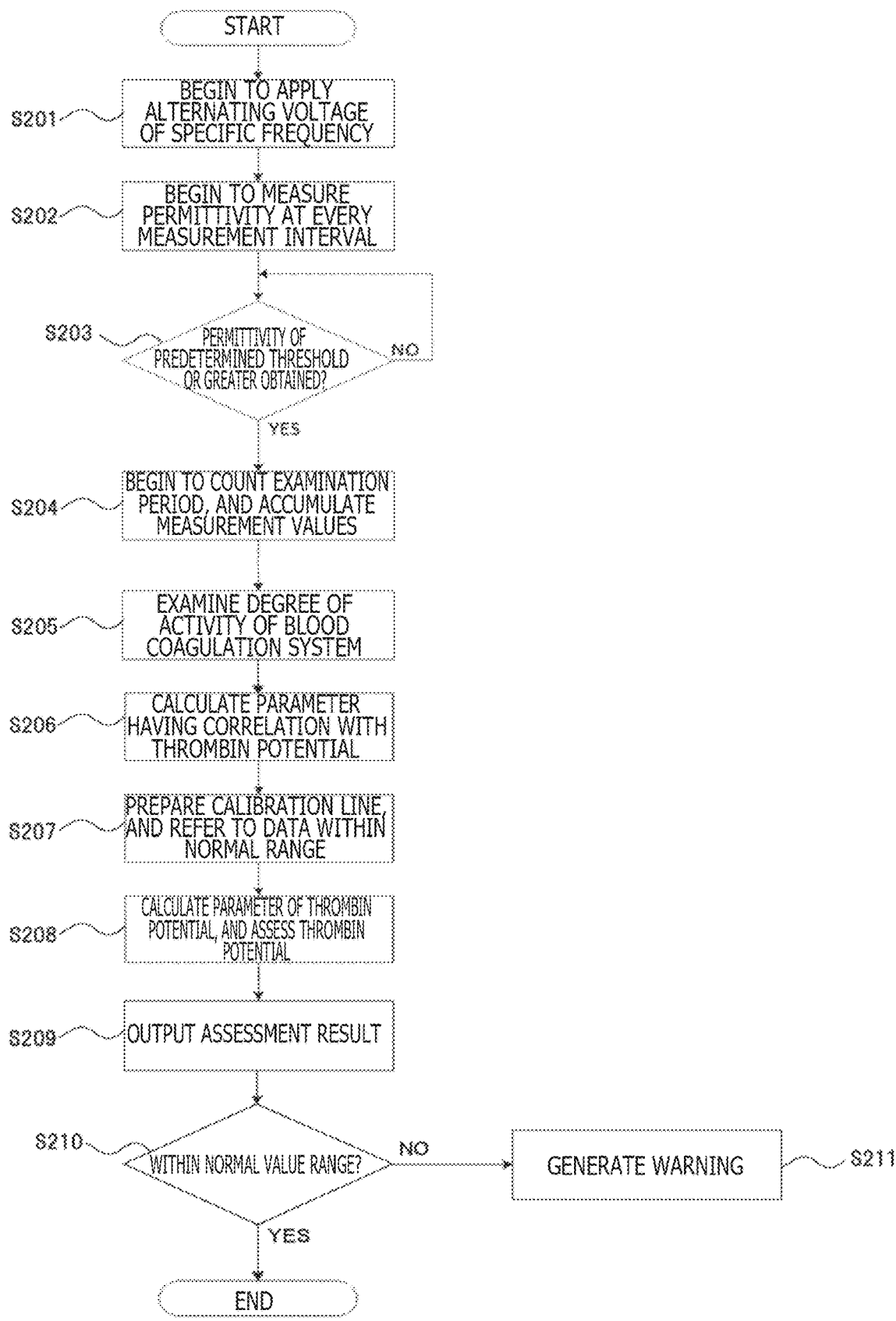
FIG. 5 is a flow chart of procedures that examine thrombin potential by a blood coagulation system examination system according to this technology.

Blood coagulation system examination procedures according to an embodiment of this technology are illustrated in the flow chart of FIG. 5.

First, blood is placed between the pair of electrodes of the blood coagulation system examination system, and an alternating voltage of a specific frequency is begun to be applied across the pair of electrodes (S201). The measurement unit measures the permittivity of the blood at every predetermined interval (S202).

The examination unit begins to examine the blood coagulation system from the permittivity so measured (S203) The examination unit holds a threshold predetermined with respect to permittivity. If permittivity data equal to or greater than the threshold is received (YES), the examination unit takes it as a time point that the anticoagulation action on the blood has been reversed, and the processing proceeds to the next step. If permittivity data smaller than the threshold is received (NO), the examination unit takes it that the anticoagulation action on the blood has not been reversed, and continues the measurement of the permittivity.

From the time point that the coagulation action on the blood has been reversed, the examination unit begins to count a preset examination period, and accumulates data of permittivity, which are fed from the measurement unit, until the examination period elapses (S204).

The examination unit detects a straight line that is most approximate to the permittivity indicated by the data of permittivity accumulated during the examination period, and examines the degree of activity of the blood coagulation system, for example, by using the gradient and/or the like of the straight line as a parameter (S205).

Next, the examination unit compares the thus-obtained parameters such as the gradient and the like with the database of thrombin potential, the database having been acquired beforehand, and calculates the parameter in terms of which the data of permittivity and the thrombin potential correlate well with each other (S206).

Further, the examination unit prepares a calibration line for converting the thus-calculated parameter into the parameter of thrombin potential (S207). The examination unit also defines a normal range of thrombin potential with reference to the database of thrombin potential.

Furthermore, the examination unit calculates the parameter of the thrombin potential from the thus-prepared calibration line (S208). The data of permittivity of the blood as the examination target are processed in terms of the parameter to assess the thrombin potential. The output unit outputs the assessment result by printing, displaying or the like (S209).

Still furthermore, the examination unit determines whether the assessment result is within the preset range of normal values of thrombin potential (S210). If it is within the range of normal values (YES), the measurement and assessment of the blood as the examination target are ended. If it is outside the range of normal values (NO), the warning unit notifies accordingly.

5-2. Determination of Parameter Correlated to Thrombin Potential

Among patients to be subjected to cardiovascular surgery, those who were 20 years of age or older and gave a document consent of his or her own free will on the basis of a thorough understanding after receiving a sufficient explanation upon participation in a clinical study were chosen, and the clinical study was conducted on them. Patients with a body weight of less than 20 kg, patients with a hematologic disorder requiring a treatment, and patients considered to feel a sense of discomfort even by small volume blood sampling due to unstable hemodynamics or the like were excluded.

Upon induction of anesthesia, immediately after the end of cardiopulmonary bypass, at entrance to the intensive care unit (ICU), after 1 week post surgery, after 3 months post surgery, and after 6 months post surgery, approximately 12 mL of blood was sampled each time from the patients. Concerning changes in total blood coagulation potential and changes in platelet function by surgical stress, a heart-lung machine, the administration of an anticoagulant, the administration of an antiplatelet agent, transfusion therapy and the like, data were acquired by conventional testing methods for the sake of reference. Extra bloods were each separated into plasma components and cell components by centrifugation, and the former components were stored in a freezer controlled at −80° C.

At a time point that a certain number of stored frozen plasma samples had been collected, they were thawed, and by using "ALC TOP" (Instrumentation Laboratory; multi-item blood coagulation analyzer), coagulation test items such as PT, APTT, FII, FV, FVIII, FIX, FX, FXI, FXII, FXIII and fibrinogen were measured. In addition, measurements by the calibrated automated thrombogram (CAT) system (Thrombinoscope Bv) were also conducted.

Figure 6:
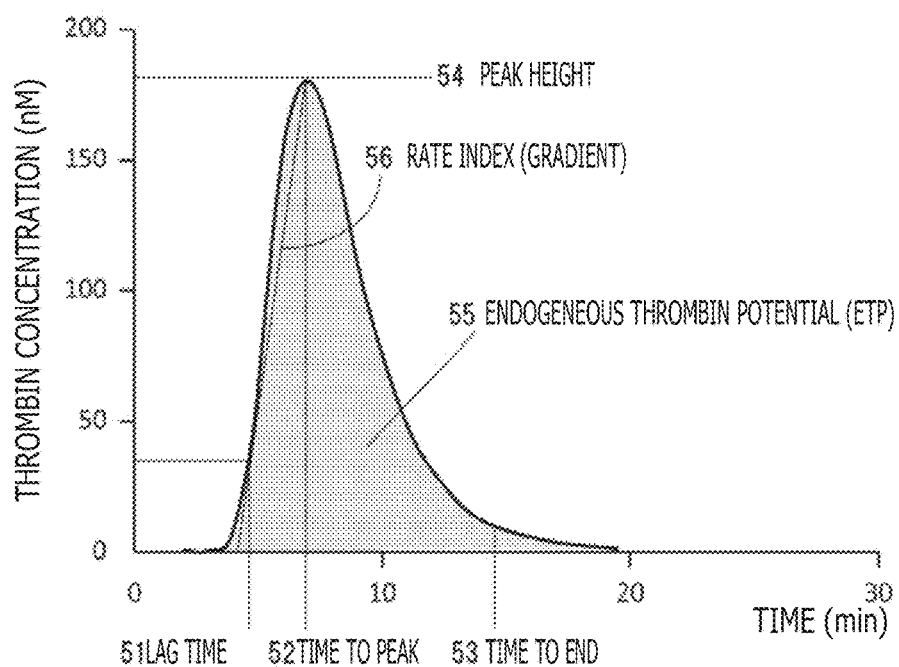
FIG. 6 is a graph illustrating a thrombin generation curve obtained from calibrated automated thrombogram.

In each calibrated automated thrombogram measurement, platelet-poor plasma (PPP) obtained by centrifugation of whole blood was used as a sample. After a calibration of fluorescence intensity was conducted following the instruction manual provided from the manufacturer, the measurement of the sample was conducted using PPP-Reagent provided from the manufacturer. PPP-Reagent contains calcium for reversing anticoagulation action by citric acid included in a blood sampling tube, and tissue factor and phospholipids for inducing an exogeneous coagulation reaction. Although not disclosed from the manufacturer, the concentration of tissue factor in PPP-Reagent is presumed to be approximately 5 pM (H. C. Hemker et al., Current Opinion in Hematology 11(3), 170-175 (2004)). A time-dependent curve of thrombin generation as obtained by the calibrated automated thrombogram method is called a "thrombogram." A thrombogram is characterized primarily by six parameters (FIG. 6).

The individual parameters of the thrombogram are described in the following Table 1.

TABLE 1

| 51 | Lag time | Time until thrombin generation starts |
| 52 | Time to peak | Time to maximum thrombin generation |
| 53 | Time to end | End time of thrombin generation |
| 54 | Peak height | Maximum value of thrombin generation amount |
| 55 | Endogenous thrombin potential (ETP) | Area under thrombin generation curve, in other words, total amount of thrombin |
| 56 | Rate index | Gradient of thrombin generation curve, in other words, thrombin generation rate |

In each measurement using the blood coagulation system examination system according to this technology, the complex permittivity was measured at 57 frequency points in a broad range of from 100 Hz to 40 MHz and intervals of 1 minute until the 60$^{th}$ minute from immediately after the beginning of the measurement to search for one or more parameters that correlate with those of the calibrated automated thrombogram system. Tissue factor was also used as an inducing substance in the measurement by the blood coagulation system examination system as in the calibrated automated thrombogram, and the measurement was conducted at various tissue factor concentrations including zero concentration (without addition of tissue factor). An assay by the blood coagulation system examination system according to this technology, which uses an anticoagulation treatment reversing agent containing calcium, tissue factor and phospholipids as in PPP-Reagent, will be called "the EX test." As the calibrated automated thrombogram measurement was conducted on the platelet-poor plasma (PPP) that platelets contributed extremely little, an assay (will be called "the PI test") that used a platelet function suppressor, which suppresses the function of platelets, in addition to the anticoagulation treatment reversing agent in the EX test was also conducted at the same time. As the platelet function suppressor, cytochalasin D was used, but "Abciximab" (trade name; "ReoPro®," Eli Lilly and Company) or the like can be also used.

Data by the blood coagulation system examination system according to this technology and data of the calibrated automated thrombogram on many samples in the clinical study were compared and considered in detail. In both an EX test and a PI test, it apparently became possible to find a parameter of the blood coagulation system examination system, which correlates with the endogeneous thrombin potential (ETP), peak height or rate index of the calibrated automated thrombogram (CAT), in a tissue factor concentration range of approximately 5 pM and lower. This correlation was presumed to become maximum especially in a tissue factor concentration range of from approximately 0.5 pM to 1 pM. When compared in terms of the combination of the same parameters, the PI test tended to result in a slightly greater correlation coefficient than the EX test. This is considered to be attributable to that the calibrated automated thrombogram as the target of the comparison was measured on the platelet-poor plasma, but does not necessarily mean that the EX test cannot be used. In the calibrated automated thrombogram (CAT) method, there is a need to select either platelet-poor plasma (PPP) or platelet-rich plasma (PRP) as a sample beforehand. With the blood coagulation system examination system according to this technology, on the other hand, on a whole blood sample, thrombin potential including the contribution by platelets can be measured by the EX test and thrombin potential under suppression of the contribution by platelets can be measured by the PI test.

As parameters of the blood coagulation system examination system that correlate with parameters of calibrated automated thrombogram, many possibilities can be contemplated, and this technology is not limited to the selection of one or a combination of particular parameters. From a study on the principle of the blood coagulation system examination system, it has been indicated that the process of the coagulation and fibrinolysis reaction can be effectively monitored by using temporally varying waveforms of real parts of permittivity at 1 MHz and 10 MHz (Y. Hayashi et al., Analytical Chemistry 87(19), 10072-10079 (2015)). Therefore, by focusing especially on waveforms at 1 MHz and 10 MHz, a search was conducted for parameters that correlate with parameters of calibrated automated thrombogram (FIG. 7 and FIG. 8).

Figure 7:
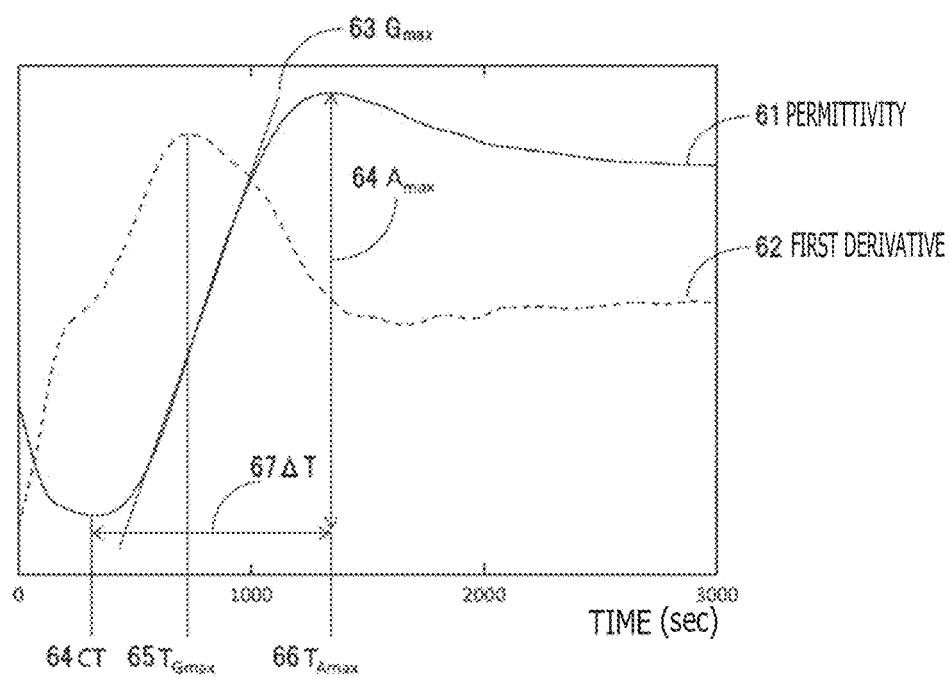
FIG. 7 is a graph illustrating a measurement result of permittivity of blood by the blood coagulation system examination system according to this technology.

FIG. 7 illustrates a typical waveform (solid line (61)) obtained as a result of a measurement at 10 MHz by the blood coagulation system examination system according to this technology, and its first derivative waveform (dashed line (62)). A time at which fibrin networks start to be formed will be called a "coagulation start time" CT (64). After the CT, the waveform begins to rise, and by way of a point (time $T_{Gmax}$ (65)) at which the gradient becomes maximum, the amplitude reaches the maximum (time $T_{Amax}$ (63)) The maximum gradient time $T_{Gmax}$ (65) is determined as a point at which the first derivative waveform reaches the maximum.

Figure 8:
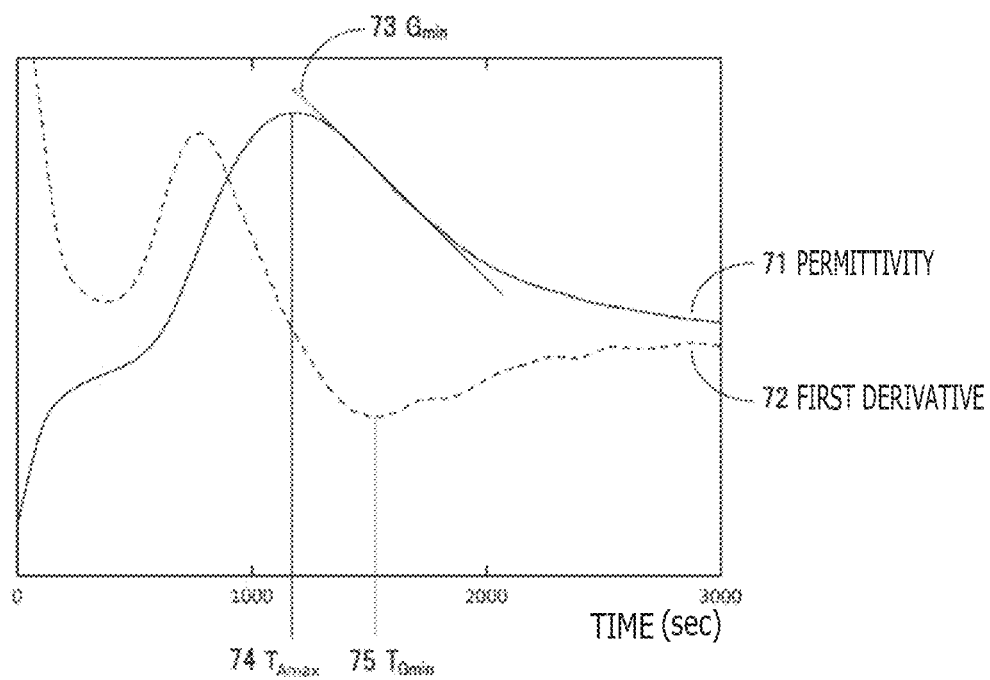
FIG. 8 is a graph illustrating a measurement result of permittivity of blood by the blood coagulation system examination system according to this technology.

FIG. 8 illustrates a typical waveform (solid line (71)) obtained as a result of a measurement at 1 MHz by the blood coagulation system examination system according to this technology, and its first derivative waveform (dashed line (72)). The waveform continues to rise from time 0 second, turns downward by way of a maximum amplitude (time $T_{Amax}$ (74)), falls at a decrease rate by way of a point (time $T_{Gmin}$ (75)) at which the gradient reaches the minimum, and eventually becomes stable. The minimum gradient time $T_{Gmin}$ (75) is determined as a point at which the first derivative waveform reaches the minimum.

Here, a value $G_{max}/A_{max}$ obtained by dividing the maximum gradient $G_{max}$ with the maximum amplitude $A_{max}$ of the 10 MHz waveform is defined as a normalized gradient, for example. Representing the blood sampling timings of upon induction of anesthesia, immediately after the end of cardiopulmonary bypass, at entrance to ICU and after 1 week post surgery in a perioperative period by A, B, C and D, respectively, the changes in the normalized gradient from A to D were found to correlate extremely well with the changes in the endogeneous thrombin potential of the same patient (FIG. 9 and FIG. 10).

FIG. 9 illustrates representative examples of changes in endogeneous thrombin potential (ETP, •) in calibrated automated thrombograms (CAT) and normalized gradient ($G_{max}/A_{max}$, ■) determined as a result of measurements by the blood coagulation system examination system according to this technology on heart surgery patients in a perioperative period. The case (top) that the overall coagulation potential decreased at the point B (immediately after the end of cardiopulmonary bypass) and the point C (at entrance to ICU) and the case (bottom) that the overall coagulation potential decreased only at the point C were also observed on other heart surgery patients. In both of the cases, the endogeneous thrombin potential and the normalized gradient presented similar changes.

FIG. 10 illustrates representative examples of changes in endogeneous thrombin potential (ETP, •) in calibrated automated thrombograms (CAT) and normalized gradient ($G_{max}/A_{max}$, ■) determined as a result of a measurement by the blood coagulation system examination system according to this technology on other heart surgery patients in a perioperative period. The case (top) that the overall coagulation potential remained relatively well over the four measurement points A to D in the perioperative period and the case (bottom) that the overall coagulation potential decreased at the point D were also observed on still other heart surgery patients. In both of the cases, the endogeneous thrombin potential ETP and the normalized gradient presented similar changes.

Figure 11:
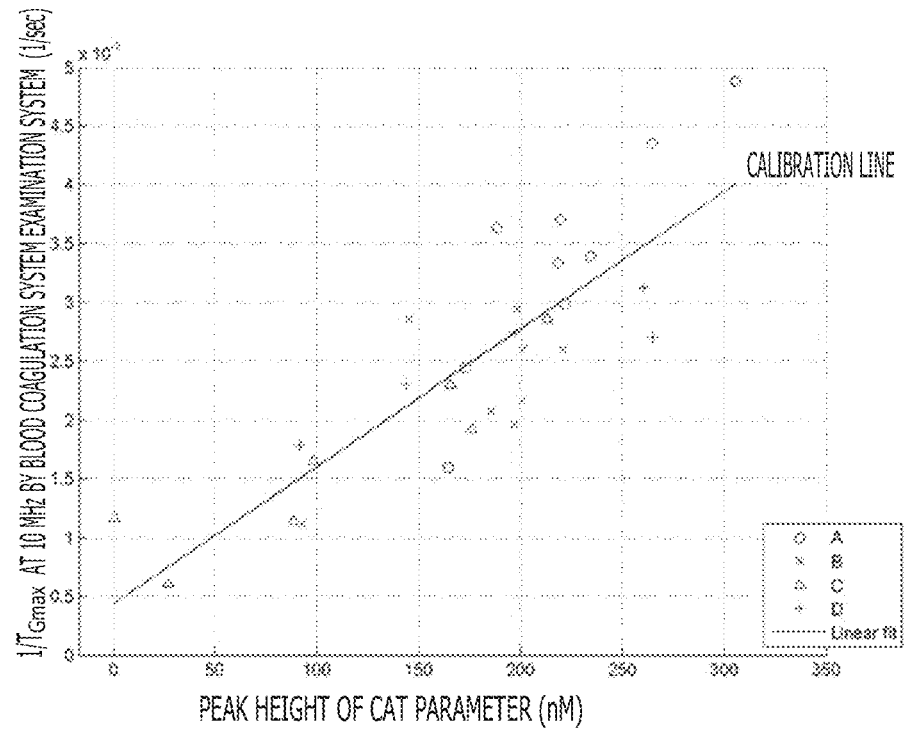
FIG. 11 is a graph illustrating a correlation between a parameter by the blood coagulation system examination system according to this technology and a parameter of calibrated automated thrombogram.
Figure 12:
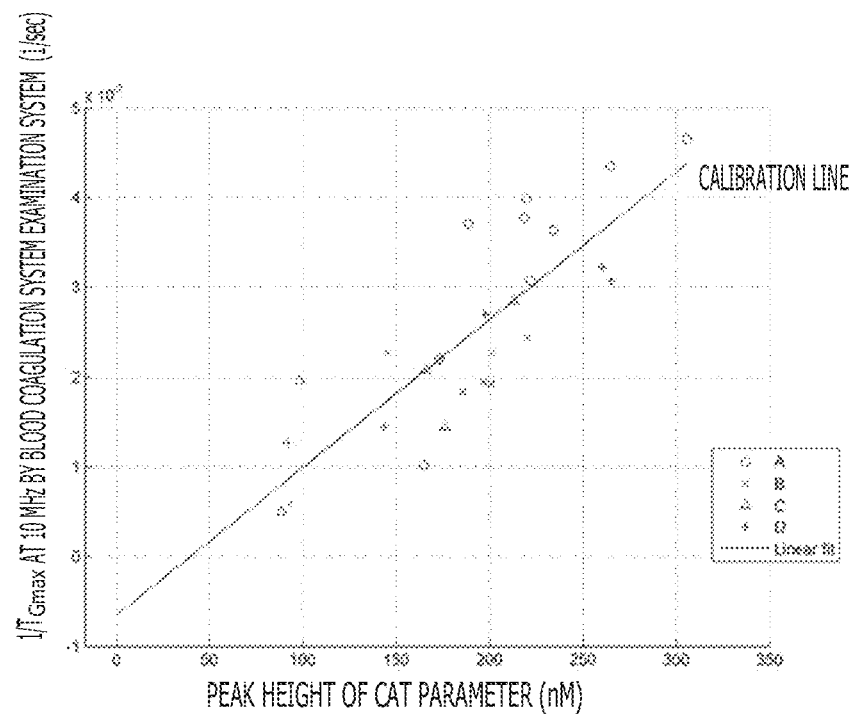
FIG. 12 is a graph illustrating a correlation between the parameter by the blood coagulation system examination system according to this technology and the parameter of calibrated automated thrombogram.

Besides the combination of the normalized gradient ($G_{max}/A_{max}$) of a 10 MHz waveform and endogeneous thrombin potential, it has also been found that the average gradient $A_{max}/\Delta T$ of the 10 MHz waveform, the reciprocal $1/T_{Gmax}$ of the time to the maximum gradient of the 10 MHz waveform, the reciprocal $1/T_{Gmin}$ of the time to the minimum gradient of a 1 MHz waveform and the reciprocal $1/T_{AMax}$ of the time to the maximum amplitude of the 1 MHz waveform each correlate with the peak height of the waveform of the endogenous thrombin potential in calibrated automated thrombograms (FIG. 11, FIG. 12).

FIG. 11 illustrates a correlation between the peak height (the abscissa) of the parameter of the calibrated automated thrombogram (CAT) and the reciprocal of the time to the maximum gradient of the 10 MHz waveform by the blood coagulation system examination system according to this technology. Data at the four measurement points A to D in the perioperative period are represented by different signs (○, x, Δ, +), and a straight line obtained by fitting all of the data in accordance with the least square method is also presented.

FIG. 12 illustrates a correlation between the peak height (the abscissa) of the parameter of the calibrated automated thrombogram (CAT) and the reciprocal of the time to the maximum amplitude of the 1 MHz waveform by the blood coagulation system examination system according to this technology. Data at the four measurement points A to D in the perioperative period are represented by different signs (○, x, Δ, +), and a straight line obtained by fitting all of the data in accordance with the least square method is also presented.

5-3. Determination of Calibration Line and Normal Range

The need for a calibration line depends on the need of a user who uses the blood coagulation system examination system according to this technology. If it is desired to obtain values in the same form as the endogenous thrombin potential and peak height in the calibrated automated thrombogram, a calibration line is needed to convert the parameters of the blood coagulation system examination system into such values. On the other hand, the preparation of a calibration line is not needed if it is sufficient insofar as a relative parameter, which varies in correlation with the thrombin potential of a patient, is obtained, for example, in a perioperative period.

As illustrated in FIG. 11 and FIG. 12 described above, the simplest preparation method of a calibration line is a method that obtains, by the least square method, an approximate straight line on a scatter plot of parameters of the calibrated automated thrombogram (CAT) and the blood coagulation system examination system according to this technology. In these examples, the data can be fitted relatively well with the straight lines. If the parameters have a more complex correlation with each other, the fitting can be conducted using an appropriate function commensurate with the complexity. If different correlations are observed depending on the range of the parameter of the calibrated automated thrombogram, fitting may be conducted by an appropriate method for every range.

If there is prior literature or the like which can be referred to for a normal range of the parameter of the calibrated automated thrombogram, its data can be used. If there are no referable data or if the use of own data is desired, a control group consisting of normal subjects is set in addition to a group of patients in a clinical study, a statistically sufficient number of data is acquired, and a normal range is determined from the data. If relative values are used without converting them into the parameter of the calibrated automated thrombogram, the normal range of the parameter of the calibrated automated thrombogram is converted into the normal range of the corresponding parameter of the blood coagulation system examination system according to this technology by using a calibration line. If own data are used, the normal range of the parameter of the blood coagulation system examination system according to this technology can also be determined directly.

The calibration line and normal range determined as described above are referred to as a database from a data examination software system in the blood coagulation system examination procedures of Step 3 mentioned above, so that reference can be made in the examination procedures newly added by this technology.

5-4. Summary

This technology takes up, for example, the thrombin potential on the basis of the new knowledge acquired through a clinical study, and adds the new examination procedures to explicitly output its parameter. From the beginning of the counting of the examination period until the accumulation of measurement values, the examination procedures for various measurement items of blood coagulation systems can be followed commonly. When measurement values have been accumulated, the new parameter specified in the above-mentioned Step 1 is calculated, and the parameter that relates to thrombin potential is calculated with reference to the database of the calibration line prepared in the above-mentioned Step 2 and the normal range, whereby it is possible to determine whether the value of the parameter is within the normal range or is an abnormal value.

The use of the examination procedures of this technology for thrombin potential makes it possible to simply, easily and swiftly acquire knowledge on thrombin potential. Consequently, even in clinical practice in which swiftness is required such as, for example, a perioperative period or emergency medical practice, the comprehensive coagulation pathophysiology of a patient can be ascertained in terms of thrombin potential. As a result, thrombosis and hemostasis treatment such as blood transfusion or anticoagulant administration can be conducted on the basis of evidence, so that the prognosis of the therapy can be improved. In addition, the volume of blood transfusion can be reduced, and therefore, a decrease of complications associated with blood transfusion or a reduction in health care cost can be realized.

Further, information associated with thrombin potential can be obtained in addition to information associated with the degree of activity of a blood coagulation system, the latter information being available by the conventional examination procedures, by simply modifying a part of a data examination software system without changes to the main body of the blood coagulation system examination system or an assay method. New introduction of thrombin potential testing equipment such as a calibrated automated thrombogram system is not needed, thereby making it possible to realize a reduction in the introduction cost for clinical testing equipment, saving of equipment installation space, or a reduction of labor in clinical practice.

This technology can adopt configurations as will be described hereinafter:

[1]

A blood coagulation system examination module including a thrombin potential examination unit configured to examine thrombin potential on a basis of an electrical property of blood as measured at a specific frequency and predetermined time intervals in a predetermined period after reversal of an anticoagulation action working on the blood.

[2]

The blood coagulation system examination module according to claim 1, in which the thrombin potential examination unit is configured to analyze a correspondence relationship between the electrical property of the blood, which has measured at the specific frequency in the predetermined period, and the thrombin potential and to examine thrombin potential of target blood from the electrical property of the target blood on a basis of the correspondence relationship.

[3]

The blood coagulation system examination module as described above in [1] or [2], in which the thrombin potential examination unit is configured to examine the thrombin potential on a basis of a value $G_{max}/A_{max}$ obtained by dividing a maximum gradient ($G_{max}$) of a waveform of the electrical property at the specific frequency in the predetermined period with a maximum amplitude ($A_{max}$) of the waveform of the electrical property at the specific frequency in the predetermined period.

[4]

The blood coagulation system examination module as described above in any one of [1] to [3], in which the blood contains tissue factor added thereto to have a concentration of 0.5 pM or higher but 1 pM or lower.

[5]

The blood coagulation system examination module as described above in any one of [1] to [4], in which the specific frequency is 1 kHz or higher but 50 MHz or lower.

[6]

A blood coagulation system examination system including:

a pair of electrodes, an application unit that applies an alternating voltage at predetermined time intervals across the pair of electrodes, a measurement unit that measures an electrical property of blood placed between the pair of electrodes, and a thrombin potential examination unit configured to examine thrombin potential on a basis of the electrical property measured at a specific frequency and the predetermined time intervals in a predetermined period after reversal of an anticoagulation action working on the blood.

[7]

The blood coagulation system examination system as described above in [6], further including an output unit that outputs information associated with the thrombin potential as examined by the thrombin potential examination unit.

[8]

The blood coagulation system examination system as described above in [7] or [8], further including a warning unit that generates a warning when a result of the examination of the thrombin potential by the thrombin potential examination unit deviates from a preset normal value.

[9]

A blood coagulation system examination method including:

applying an alternating voltage at the predetermined time intervals across a pair of electrodes, measuring an electrical property of blood placed between the pair of electrodes, and examining thrombin potential on a basis of the electrical property measured at a specific frequency and the predetermined time intervals in a predetermined period after reversal of an anticoagulation action working on the blood.

[10]

A determination method of a parameter for a blood coagulation system examination module, including:

applying an alternating voltage at the predetermined time intervals across a pair of electrodes, measuring an electrical property of blood placed between the pair of electrodes, and determining the parameter for examination of thrombin potential by comparing data, which are obtained from the electrical property measured at a specific frequency and the predetermined time intervals in a predetermined period after reversal of an anticoagulation action working on the blood, with data obtained in a known test on the thrombin potential.

REFERENCE SIGNS LIST

2: Application unit
3: Power supply
11, 12: Electrode
41: Measurement unit
42: Examination unit
43: Output unit
44: Warning unit
51: Lag time
52: Time to peak
53: Time to end
54: Peak height
55: Endogeneous thrombin potential
56: Rate index

The invention claimed is:

1. A blood coagulation system examination module comprising a thrombin potential examination unit configured to examine thrombin potential on a basis of an electrical property of blood as measured at a specific frequency and predetermined time intervals in a predetermined period after reversal of an anticoagulation action working on the blood.

2. The blood coagulation system examination module according to claim 1, wherein the thrombin potential examination unit is configured to analyze a correspondence relationship between the electrical property of the blood, which has measured at the specific frequency in the predetermined period, and the thrombin potential and to examine thrombin potential of target blood from the electrical property of the target blood on a basis of the correspondence relationship.

3. The blood coagulation system examination module according to claim 1, wherein the thrombin potential examination unit is configured to examine the thrombin potential on a basis of a value $G_{max}/A_{max}$ obtained by dividing a maximum gradient ($G_{max}$) of a waveform of the electrical property at the specific frequency in the predetermined period with a maximum amplitude ($A_{max}$) of the waveform of the electrical property at the specific frequency in the predetermined period.

4. The blood coagulation system examination module according to claim 1, wherein the blood contains tissue factor added thereto to have a concentration of 0.5 pM or higher but 1 pM or lower.

5. The blood coagulation system examination module according to claim 1, wherein the specific frequency is 1 kHz or higher but 50 MHz or lower.

6. A blood coagulation system examination system comprising:

a pair of electrodes, an application unit that applies an alternating voltage at predetermined time intervals across the pair of electrodes, a measurement unit that measures an electrical property of blood placed between the pair of electrodes, and a thrombin potential examination unit configured to examine thrombin potential on a basis of the electrical property measured at a specific frequency and the predetermined time intervals in a predetermined period after reversal of an anticoagulation action working on the blood.

7. The blood coagulation system examination system according to claim 6, further comprising an output unit that outputs information associated with the thrombin potential as examined by the thrombin potential examination unit.

8. The blood coagulation system examination system according to claim 6, further comprising a warning unit that generates a warning when a result of the examination of the thrombin potential by the thrombin potential examination unit deviates from a preset normal value.

9. A blood coagulation system examination method comprising:
applying an alternating voltage at predetermined time intervals across a pair of electrodes,
measuring an electrical property of blood placed between the pair of electrodes, and
examining thrombin potential on a basis of the electrical property measured at a specific frequency and the predetermined time intervals in a predetermined period after reversal of an anticoagulation action working on the blood.

10. A determination method of a parameter for a blood coagulation system examination module, comprising:
applying an alternating voltage at predetermined time intervals across a pair of electrodes,
measuring an electrical property of blood placed between the pair of electrodes, and
determining the parameter for examination of thrombin potential by comparing data, which are obtained from the electrical property measured at a specific frequency and the predetermined time intervals in a predetermined period after reversal of an anticoagulation action working on the blood, with data obtained in a known existing test on the thrombin potential.

* * * * *